(12) United States Patent
Sokal

(10) Patent No.: US 8,132,566 B2
(45) Date of Patent: Mar. 13, 2012

(54) VAS DEFERENS VASECTOMY CAPPING DEVICE

(75) Inventor: David C. Sokal, Durham, NC (US)

(73) Assignee: Family Health International, Durham, NC (US)

( * ) Notice: Subject to any disclaimer, the term of this patent is extended or adjusted under 35 U.S.C. 154(b) by 191 days.

(21) Appl. No.: 12/235,727

(22) Filed: Sep. 23, 2008

(65) Prior Publication Data

US 2009/0078271 A1 Mar. 26, 2009

Related U.S. Application Data

(60) Provisional application No. 60/975,093, filed on Sep. 25, 2007.

(51) Int. Cl.
*A61F 6/00* (2006.01)

(52) U.S. Cl. .................. 128/843; 128/842; 606/157

(58) Field of Classification Search .......... 128/842–843, 128/918, 830–832, 885, 887; 604/34, 41, 604/96.01, 215, 266, 907, 256, 8, 9, 332, 604/337; 606/157, 152, 153; 600/29–32; 424/430

See application file for complete search history.

(56) References Cited

U.S. PATENT DOCUMENTS

| | | | |
|---|---|---|---|
| 3,880,137 A * | 4/1975 | Bucalo | 128/843 |
| 3,938,499 A | 2/1976 | Bucalo | |
| 3,938,528 A * | 2/1976 | Bucalo | 128/843 |
| 3,951,132 A | 4/1976 | Bucalo | |
| 3,954,108 A | 5/1976 | Davis | |
| 4,050,448 A | 9/1977 | Borgen | |
| 4,135,495 A | 1/1979 | Borgen | |
| 4,200,088 A * | 4/1980 | Denniston, Jr. | 128/843 |
| 4,200,107 A | 4/1980 | Reid | |
| 4,245,638 A | 1/1981 | Lebeck et al. | |
| 4,380,238 A | 4/1983 | Colucci et al. | |
| 4,394,864 A | 7/1983 | Sandhaus | |
| 4,576,161 A | 3/1986 | Mikkelson | |
| 4,682,598 A | 7/1987 | Beraha | |
| 4,693,251 A | 9/1987 | Bleier et al. | |
| 4,817,602 A | 4/1989 | Beraha | |
| 4,860,746 A | 8/1989 | Yoon | |
| 5,067,958 A | 11/1991 | Sandhaus | |
| 5,471,997 A | 12/1995 | Thompson | |
| 5,575,802 A | 11/1996 | McQuilkin et al. | |
| 5,611,794 A | 3/1997 | Sauer et al. | |
| 5,618,305 A | 4/1997 | Lolagne | |
| 5,667,518 A | 9/1997 | Pannell | |
| 5,746,222 A * | 5/1998 | Simon et al. | 128/885 |
| 6,432,116 B1 | 8/2002 | Callister et al. | |
| 6,513,528 B2 | 2/2003 | Burton et al. | |
| 6,602,250 B2 | 8/2003 | Karpiel et al. | |

(Continued)

OTHER PUBLICATIONS

Aradhya, K.W., et al., "Recent developments in vasectomy," bmj.com, 330(7486): 296-299 (2005).

(Continued)

*Primary Examiner* — Patricia Bianco
*Assistant Examiner* — Keri J Nelson
(74) *Attorney, Agent, or Firm* — Womble Carlyle Sandridge & Rice, LLP

(57) ABSTRACT

A medical device is provided which forms a physical barrier between the two ends of a cut vas during a vasectomy procedure, comprising a biodegradable, polymeric cap that is applied over at least one prostatic end of the vas, the cap including a fastener for preventing premature dislodgement.

5 Claims, 6 Drawing Sheets

U.S. PATENT DOCUMENTS

| | | |
|---|---|---|
| 6,607,522 B1 | 8/2003 | Hamblin et al. |
| 6,740,098 B2 | 5/2004 | Abrams et al. |
| 6,746,461 B2 | 6/2004 | Fry |
| 6,794,485 B2 | 9/2004 | Shalaby et al. |
| 6,852,082 B2 | 2/2005 | Strickberger et al. |
| 2001/0041900 A1 | 11/2001 | Callister et al. |
| 2002/0029051 A1 | 3/2002 | Callister et al. |
| 2002/0072759 A1 | 6/2002 | Fry |
| 2003/0051735 A1 | 3/2003 | Pavcnik et al. |
| 2005/0085844 A1 | 4/2005 | Tremulis et al. |
| 2005/0217680 A1 | 10/2005 | Callister et al. |

OTHER PUBLICATIONS

Barone, M.A., et al., "Effectiveness of vasectomy using cautery," BMC Urology, 4:10 (2004).

Chen-Mok, M., et al., "Termination of randomized controlled trial of two vasectomy techniques," Controlled Clinical Trials, 24(2): 78-84 (2003).

Deneux-Tharaux, C., et al., "Pregnancy rates after vasectomy: a survey of US urologists," Contraception 69: 401-406 (2004).

Labrecque, M., et al., Comment on "How little is enough? The evidence for post-vasectomy testing," J. Urol. 174(1): 29-36, (2005); J. Urol. 175(2); 791-792 (2006).

Nazerali, H., et al., "Vasectomy effectiveness in Nepal: a retrospective study," Contraception, 67(5): 397-401 (2003).

Rhodes, D.B., et al., "Vasectomy: efficacy of placing the cut vas in different fascial planes," Fertility and Sterility, 33(4): 433-438 (1980).

Sokal, D.C., "Recent research on vasectomy techniques." Asian J. Androl., 5(3): 227-230 (2003).

Wood, B.L., et al., "Effect of diltiazem and methylene blue on human sperm motility, viability and cervical mucus penetration: potential use as vas irrigants at the time of vasectomy," Contraception 67(3): 241-245 (2003).

* cited by examiner

VAS DEFERENS VASECTOMY CAPPING DEVICE

RELATED APPLICATIONS

This application claims the benefit of U.S. Provisional Application No. 60/975,093, filed Sep. 25, 2007.

FIELD OF THE INVENTION

The present invention relates to the surgical technique of vasectomy, and, in particular, a device which covers and occludes the cut ends of the vas during the vasectomy procedure.

BACKGROUND OF THE INVENTION

Vasectomy is a surgical procedure that interrupts the continuity of the vas deferens (vas) in order to prevent sperm from passing from the testis into the ejaculate, thus preventing sperm from uniting with the ova. Vasectomy is the most effective contraceptive method available to men. While vasectomy is considered to be a permanent procedure, it can be reversed with varying degrees of success.

There are many surgical techniques that have been devised for vasectomies, with varying degrees of effectiveness. Recent research has confirmed that fascial interposition increases the effectiveness of ligation and excision, and the lowest failure rates for vasectomy have been reported by physicians using a combination of cautery and fascial interposition. As used herein, "fascial interposition" refers to the surgical technique of interposing a layer of fascial membrane, from the fascial sheath which surrounds the vas, between the two cut ends of the vas.

The inventors have found that the most common cause of vasectomy failure is early recanalization. As used herein, "recanalization" refers to the spontaneous regrowth of one or more tubules between the cut ends of the vas deferens. It occurs most commonly within three weeks to two months after vasectomy and is diagnosed by the successful passage of sperm from the testes into the semen.

When properly done, fascial interposition prevents recanalization by interposing a tissue barrier between the cut ends of the vas. However, the surgical technique of fascial interposition is time-consuming and requires considerable surgical skill. Many surgeons consider fascial interposition to be too difficult. In addition, fascial interposition may be difficult to implement in men who have a history of bacterial infections such as sexually transmitted infections, or parasitic infections, such as filariasis, which may cause fibrotic changes in scrotal tissues.

SUMMARY OF THE INVENTION

To improve and facilitate vasectomy procedures, an easier, more reliable way of doing fascial interposition is the present invention, which provides a device in the form of a biodegradable, fluid impermeable polymeric cap that takes the place of fascial interposition. Rather than relying on the manipulation of delicate and variable tissue layers, this cap provides an impermeable barrier between the two ends of the cut vas. This invention provides a device that takes the place of fascial interposition.

More particularly, the device is a vas deferens cap (vasectomy cap), which when applied to the vas, provides a physical barrier to cover the cut end of one or both ends of the vas. In one embodiment, the vasectomy cap covers only the abdominal or prostatic end of the vas. The vasectomy cap may, however, be applied with a hand-held applicator that simultaneously cuts the vas and clamps the device over both ends of the cut vas.

The essential functionality of the vasectomy cap is two-fold:
a) the vasectomy cap provides an impermeable barrier that prevents early recanalization of the vas; and
b) the vasectomy cap includes one or more features to prevent dislodgement, such as anchoring teeth and/or a provision for a suture or one or more hooks that would pass through the vas and anchor the device to the vas.

In an embodiment, the device is formed of a polymeric material that is bio-compatible, such as a biodegradable plastic. The vasectomy cap is preferably of low stiffness, with enough flexibility so as not to erode either the vas or other surrounding tissue layers, but with stiffness sufficient to grip the vas as described below. Suitable polymer/copolymer types include, but are not limited to, polyureas, polyurethanes, poly(ethylene/-vinyl acetate), polyvinylchloride, polyesters, polyamides, polycarbonate, polyethylene, polypropylene, polystyrenes, polytetrafluoroethylene, polyhydroxyalkanoates, and silicone. The device may be stiffer at the surface covering the cut end of the vas, and more flexible at the end furthest from the cut end of the vas.

The vasectomy cap may be applied to the vas by surgeons using either a no-scalpel vasectomy (NSV) technique or a standard incision technique. These two techniques are slightly different ways to approach the vas and bring a loop of the vas outside of the scrotum, also referred to as isolating the vas. This constitutes the first part of the vasectomy procedure, prior to the step of occluding the vas. With the NSV technique, a ringed clamp is used to fix the vas through the scrotal skin, and then the dissecting forceps are used to puncture the skin, spread open the puncture, grasp the vas, and then bring a loop of the vas outside the scrotal skin. The NSV technique involves the exposure and isolation of a small loop of the vas, which is usually a shorter length than exposed by the standard incision technique. However, the vasectomy cap may be used to occlude the vas irrespective of which technique is used to approach and isolate a loop of the vas.

These and other aspects of the present invention will become apparent to those skilled in the art after a reading of the following description of exemplary embodiments when considered in conjunction with the drawings. It should be understood that both the foregoing general description and the following detailed description are exemplary and explanatory only and are not restrictive of the invention as claimed.

DETAILED DESCRIPTION

The present invention is directed to a device for capping one or both exposed ends of the vas lumen that are cut during a vasectomy procedure. The vasectomy cap attaches to the vas and serves as a cap to cover one or both ends of the vas, thus preventing early recanalization. The vasectomy cap can be applied by a hand-held surgical instrument (applicator) that also may be used to cut the vas.

In the course of a vasectomy, the surgeon creates an opening through the skin of the scrotum and pulls a loop of the vas and fascial tissues outside the scrotum. He then removes extraneous fascial tissues from the vas. Once a loop of the vas has been clearly identified and isolated, the vasectomy cap is applied.

Figure 2:
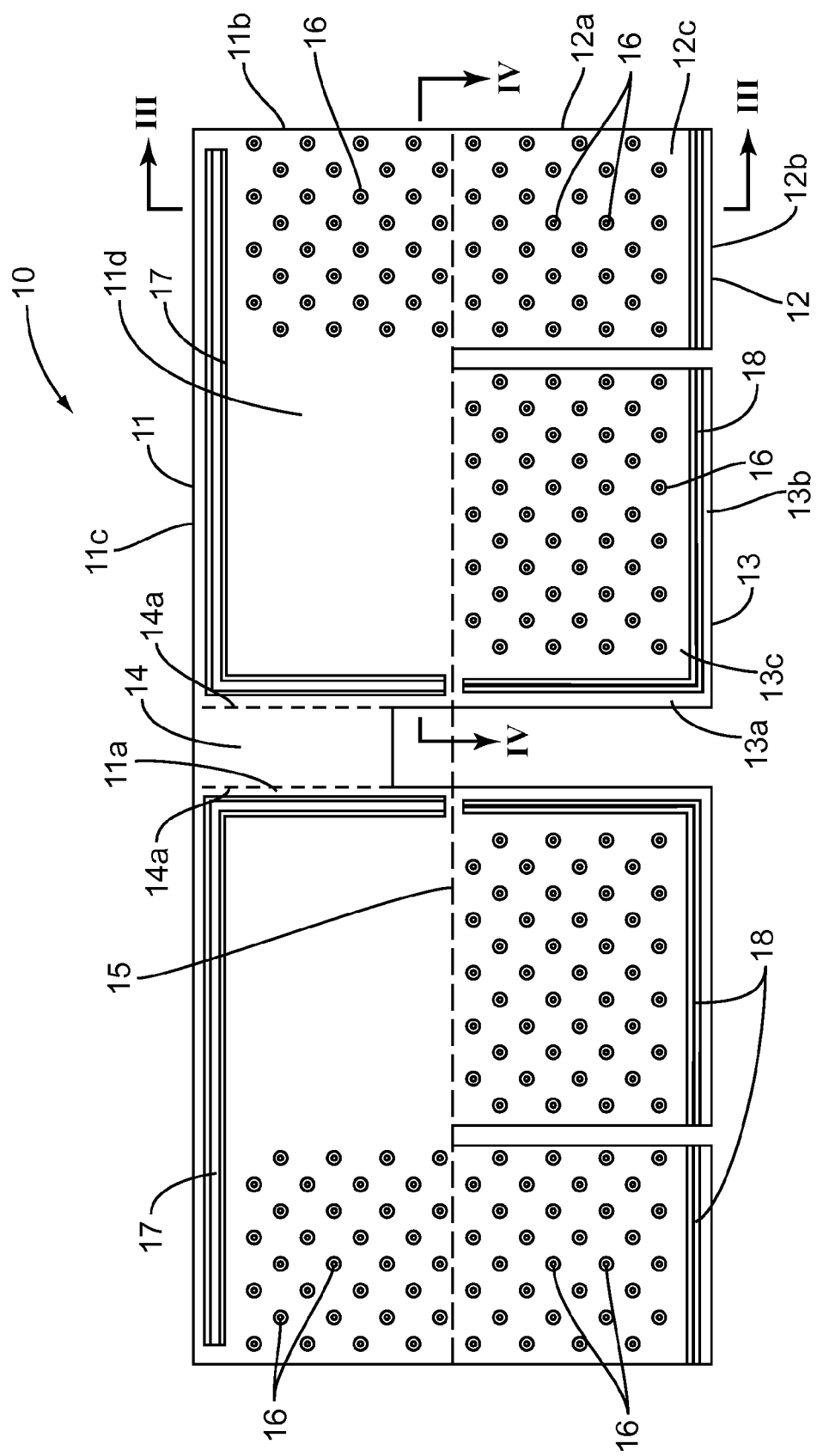
FIG. 2 is a top view of the device lying flat.

Referring to the Figures in general, and FIG. 2 in particular, one embodiment of the device for capping the open ends of the vas lumen is shown generally as 10. As shown in FIG. 2, the device 10 is lying flat in a ready to apply configuration. The embodiment shown in FIG. 2 comprises two symmetrical portions, and thus two caps. The symmetrical portions each comprise three flaps, which are identical mirror images of each other on the right and left portions. These include a main rectangular body flap 11, a rectangular first flap 12, and a rectangular second flap 13. The two symmetrical portions are removably connected along cut lines 14*a* by an intermediate connector 14. The cut lines 14*a* may also initially serve as fold lines during application of the device. A further fold line 15 also separates the main body flap 11 from the first flap 12 and second flap 13. Fold line 15 allows the first flap 12 and second flap 13 to be folded onto the inner surface of the main body flap 11, as will be explained in greater detail below.

Each main body flap 11 comprises a proximal end 11*a* adjacent the intermediate connector 15, an opposed distal end 11*b*, a forward edge 11*c*, an inner surface 11*d*, and a fastener element 17 along the proximal end 11*a* and the forward edge 11*c*. A plurality of spaced-apart barbs 16 are formed on the distal portion of the inner surface 11*c*. The first flap 12 comprises a distal end 12*a*, a rearward edge 12*b*, an inner surface 12*c*, and a faster element 18 along the rearward edge 12*b* for subsequent mating engagement with fastener element 17. A plurality of spaced-apart barbs 16 are formed substantially over the entire inner surface 12*c*. The second flap 13 comprises a proximal end 13*a*, a rearward edge 13*b*, an inner surface 13*c*, and a fastener element 18 along the proximal end 13*a* and rearward edge 13*b* for subsequent engagement with fastener element 17. A plurality of spaced-apart barbs 16 are formed substantially over the entire inner surface 13*c*.

Figure 3:
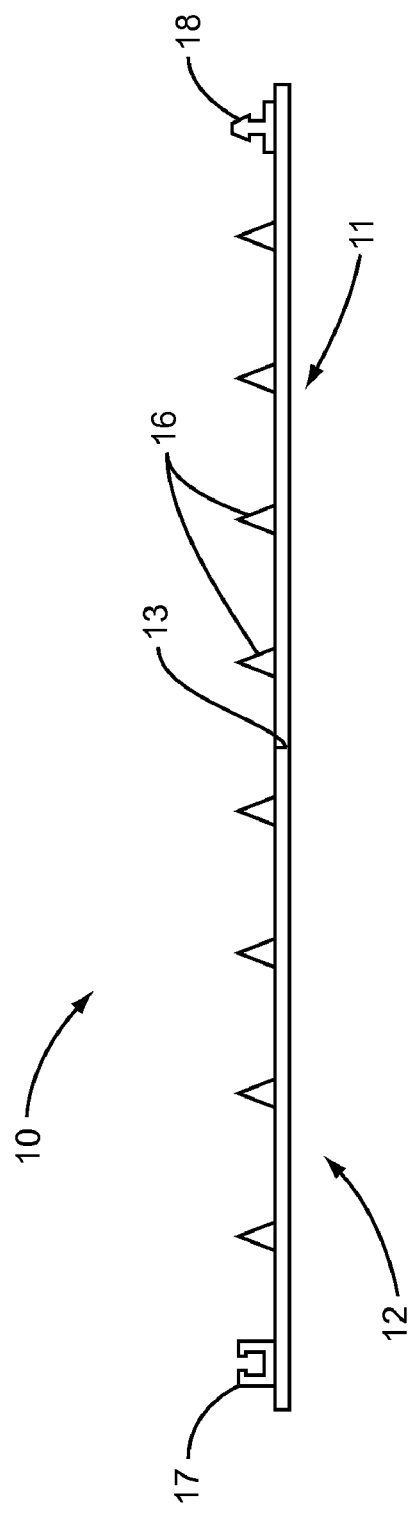
FIG. 3 is a side elevational, cross-sectional view of the device of FIG. 2, taken along lines II-II.

FIG. 3 illustrates the cross-section of the embodiment 10 illustrated in FIG. 2 through the first flap 12 and the main body flap 11. One exemplary type of fastener comprises interlocking rib 17 and groove 18 fastener elements; however, other suitable fasteners known to those skilled in the surgical arts may be used.

Figure 4:
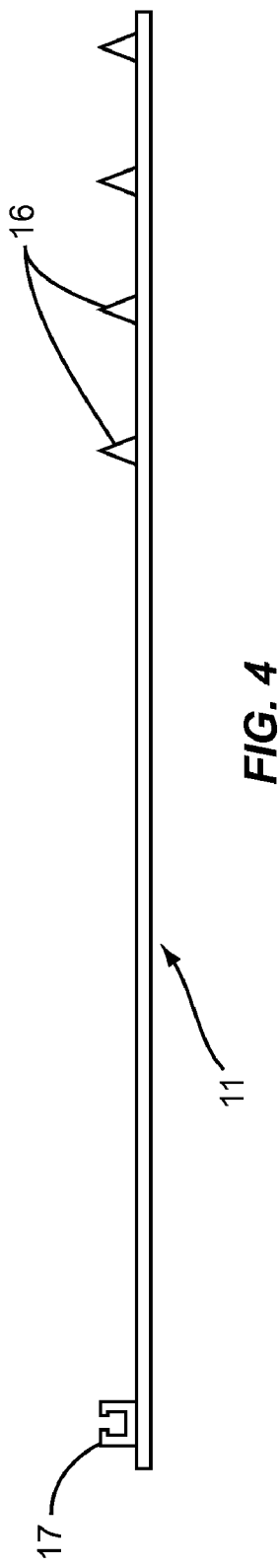
FIG. 4 is a side elevational, cross-sectional view of the device of FIG. 2, taken along lines III-III.

FIG. 4 illustrates the cross-section through the main body flap 11, and shows the shape of one form of interlocking groove 17 fastener element. FIG. 4 also illustrates the attachment points or barbs 16, which cover the distal portion of the main body 11 opposite the first flap 12, but which are not present on the surface opposite the second flap 13.

When pressure is exerted to close the flaps 12, 13 against the main body flap 11, the edges of the flaps become bound to the main body by the engagement of the interlocking rib 17 and groove 18 fastener elements. The locations of the rib 17 and groove 18 fastener elements could be switched, with no change in function or effectiveness, and other engagement mechanisms could be used by those skilled in the art of medical device design.

Figure 1A:
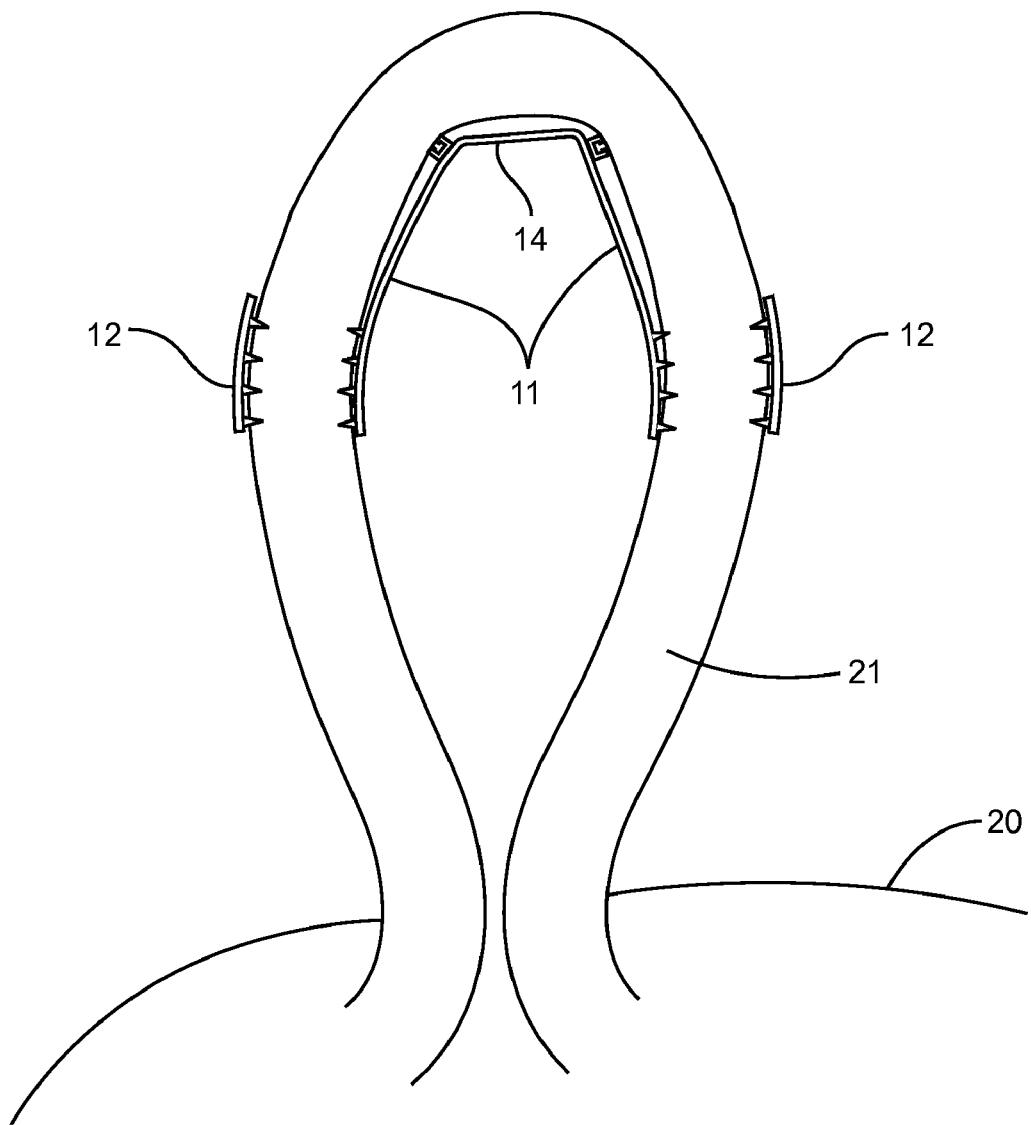
FIG. 1A is a cross-sectional view of the device being applied to the vas, with a first flap wrapped around each side.
Figure 1B:
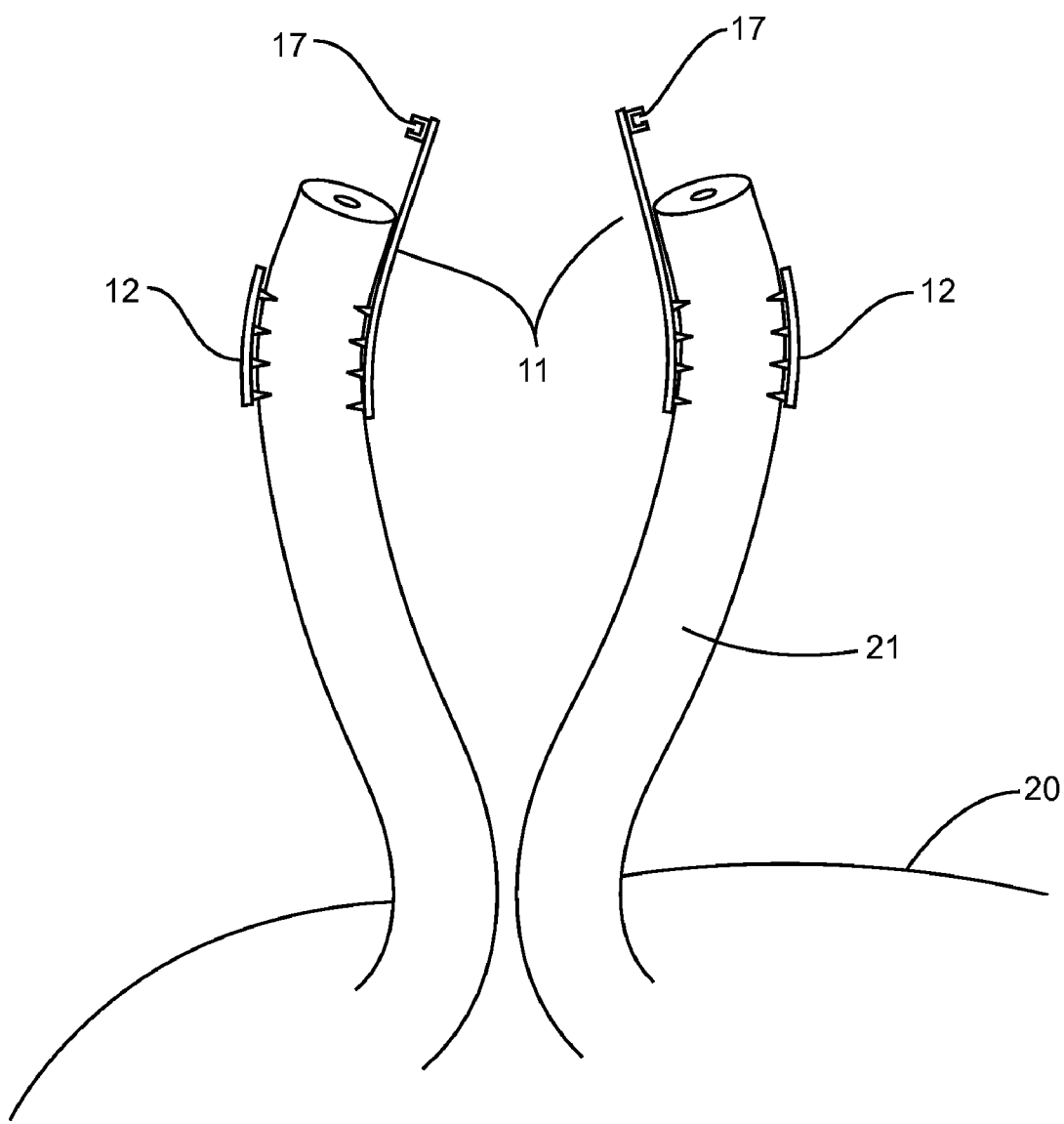
FIG. 1B is a cross-sectional view of the device after the vas has been cut.
Figure 1C:
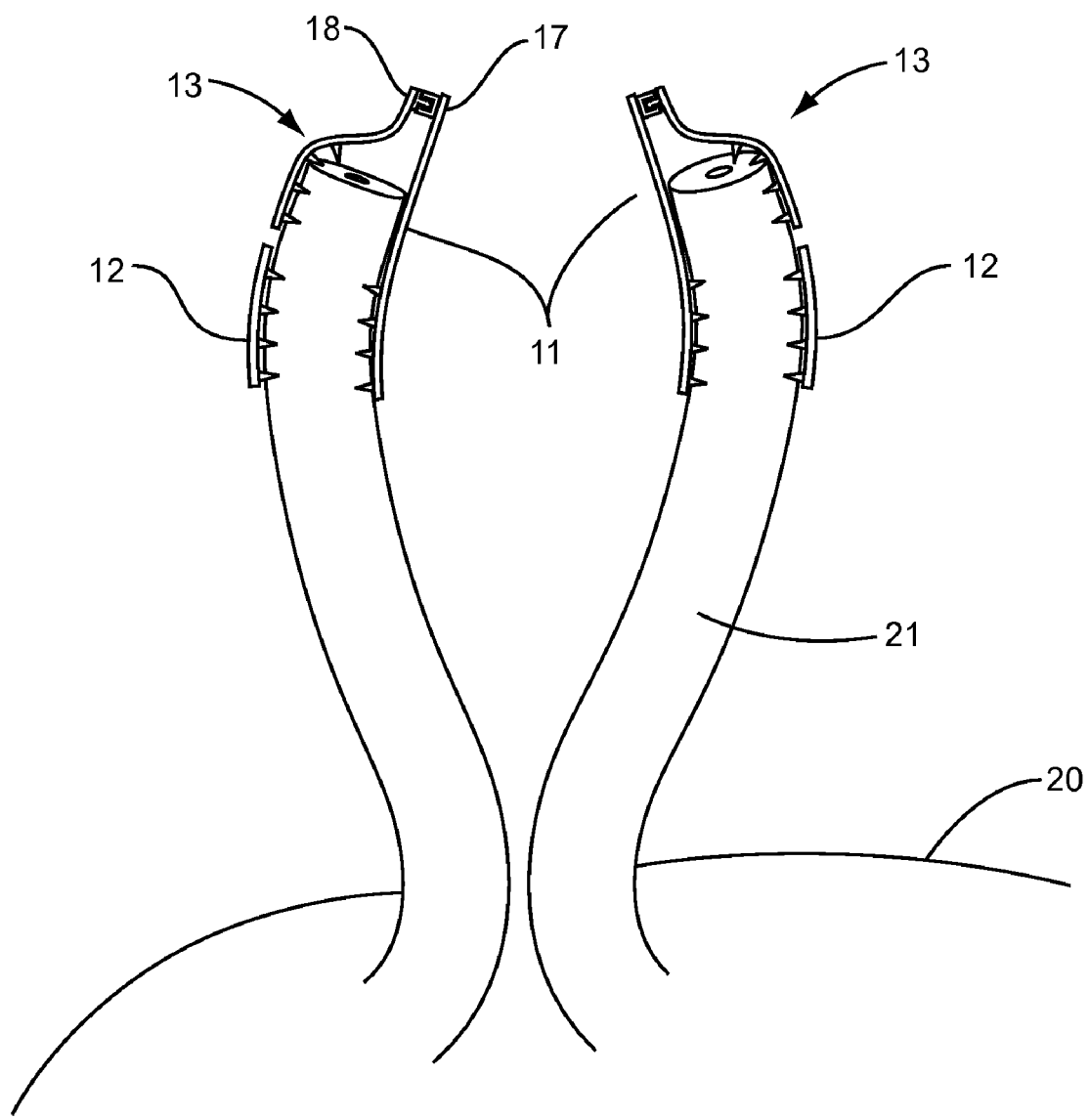
FIG. 1C is a cross-sectional view of the device after a second flap is wrapped around each side.

Turning to FIGS. 1A through 1C, application of the device is illustrated. FIG. 1A illustrates how the device is positioned around the vas, either manually or with an applicator. As shown in the Figure, the device is placed with the two symmetrical portions on either side of the loop 21, separated by the intermediate connector. The main body flap 11 is fitted inside the loop 21 and anchored with barbs 16. The first flap 12 is then closed over the loop 21 and anchored. The second flap 13 has been folded beneath main body flap 11 for this step.

After this is done, two parallel cutting blades are used to cut the device 10 along vasectomy cap along the fold lines 14*a* on either side of the intermediate connector piece 14, as well as cutting and removing a short segment of the vas loop 21. Alternatively, two separate cuts could be made using scissors or a scalpel. An advantage of this technique is that the surgeon will have a small segment of the vas loop 21 to send to a pathologist for histological examination, in order to verify that the correct structure was cut. Many surgeons do this in order to document that the surgery was performed correctly.

FIG. 1B shows the device 10 and the vas loop 21 after the cutting operation is complete. Because the vas loop 21 is under tension and is stretched when it is pulled from the scrotum 20, it will retract after being cut, but the barbs 16 prevent the vas from retracting back into the scrotum 20. However, the distal inner surface of main body flap 11 does not have barbs, thus permitting the cut vas 21 to retract slightly so that the second flap 13 may be folded over, anchored, and secured with fastener elements 17, 18.

Lastly, FIG. 1C shows each symmetrical portion after the second flap 13 has been folded and engaged with the main body flap 11 via the fastening elements 17, 18.

The size of the device 10 is adapted to fit around the vas. The outside diameter of the vas in adult males ranges from approximately 1.5 to 3.0 mm in diameter, or a circumference ranging from between about 4.5 and 9.5 mm. Thus, the width of each symmetrical portion to accommodate the largest vas diameter should be between about 12 and 14 mm. This would allow each portion to encircle the vas. Two or three different widths could be made to best accommodate the variation in the size of the vas. The length of each side, such as the length of side 11*c*, could be from about between 1 and 2 cm.

Figure 5:
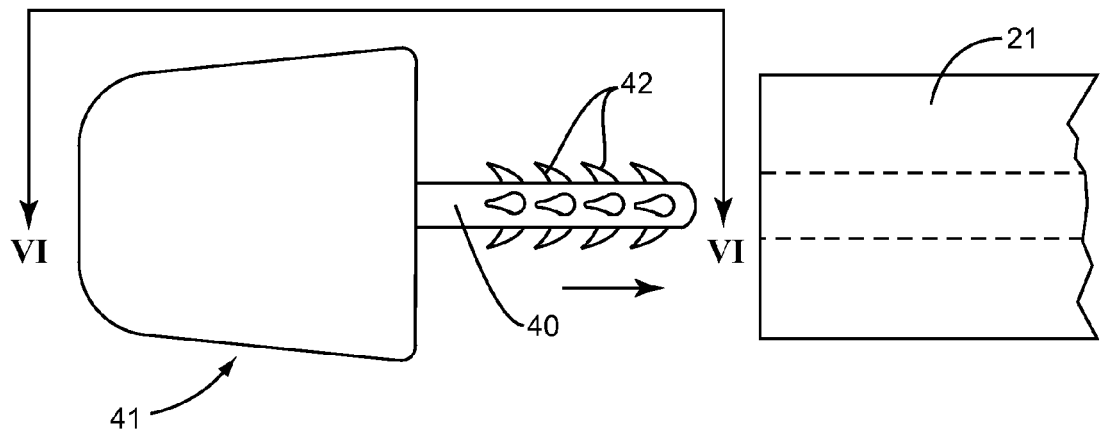
FIG. 5 is an alternative embodiment of a vasectomy cap.
Figure 6:
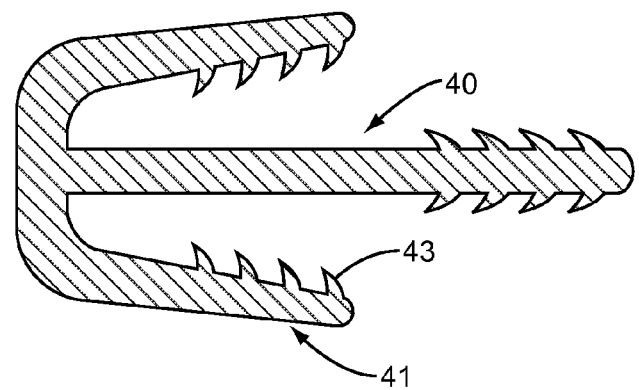
FIG. 6 is a cross-sectional view of the embodiment of FIG. 5, taken along lines VI-VI.

FIGS. 5 and 6 illustrate an alternate embodiment of the vas cap, with a linear post 40 with barbs 42 that are inserted into the lumen of the vas, and a cap 41 that covers the end of the vas 21. Supplemental barbs 43 also may be formed inside the cap 41 to provide additional attachment to the vas 21.

Since the vas develops a point of fibrosis following vas occlusion due to the tissue reaction provoked by sperm that are no longer contained in the vas, the vas cap could be made of a biodegradable polymer that would disintegrate and be completely metabolized within about 3 to 12 months after the procedure. As described above, various type of biodegradable polymers may be used having the desired characteristics, including polymers and co-polymers chosen from among the following types: poly(dl-lactide), poly(l-lactide), polyglycolide, poly(dioxanone), poly(glycolide-co-trimethylene carbonate), poly(l-lactide-co-glycolide), poly(dl-lactide-co-glycolide), poly(l-lactide-co-dl-lactide), poly(glycolide-cot-rimethylene, and polyhydroxyalkanoates.

Although the present invention has been described with an exemplary embodiment, it is to be understood that modifications and variations may be utilized without departing from the spirit and scope of the invention, as those skilled in the art will readily understand. Such modifications and variations are considered to be within the purview and scope of the appended claims and their equivalents. For instance: The device could be impregnated or coated with an anti-infective agent. The surfaces of the device could be roughened so that it can be easily visualized after implantation by sonic imaging equipment. The device could be made radio-opaque by the blending of radio-opaque material in the plastic polymer; e.g., silver particles or other agents known to those skilled in the medical device arts, so that it can be easily visualized after implantation by X-ray imaging techniques. The device could made visible to magnetic resonance imaging techniques by the inclusion of ferromagnetic or paramagnetic particles in the plastic as known to those skilled in the medical device arts, so that it can be easily visualized after implantation. Additionally, in lieu of barbs, the device could be anchored with other types of securing elements such as a medical glue or tissue adhesive, through the use of sutures, clamps, or others.

I claim:

1. A medical device that provides a physical barrier between the two ends of a cut vas during a vasectomy procedure, comprising a cap that is applied over at least one end of the cut vas, the cap having a completely closed top, an open bottom, and a continuous substantially cylindrical side wall extending therebetween defining an inner volume, the cylindrical side wall being of such length that, when emplaced, extends down the length of the vas a prescribed sufficient distance and the inner surface of the cylindrical side wall including a plurality of fastener elements extending inwardly therefrom toward the exterior surface of the vas that, when emplaced, engage the vas, the side wall and fastener elements both preventing premature dislodgement.

2. The device of claim 1 further comprising a post formed within the inner volume and extending downwardly from the closed top, the post dimensioned for insertion into the open end of the vas, the post having an outer surface.

3. The device of claim 2 further comprising a plurality of barbs formed on the outer surface of the post, the plurality of barbs having tips angled upwardly toward the closed top.

4. A device for capping at least the exposed prostatic end of a vas lumen cut during a vasectomy procedure, comprising:
   (a) a cap having a completely closed top, an open bottom, and a continuous cylindrical side wall having an inner surface and extending therebetween defining an inner volume, the cap dimensioned to fit over the open prostatic end of the vas lumen and the cylindrical side wall being of such length that, when emplaced, extends down the length of the vas a prescribed distance;
   (b) a plurality of barbs formed on the inner surface, the plurality of barbs having tips angled upwardly toward the closed top, having tips angled upwardly toward the closed top, whereby the length of the side wall and the plurality of barbs prevent premature dislodgement;
   (c) a post formed within the inner volume and extending downwardly from the closed top, the post dimensioned for insertion into the open lumen, the post having an outer surface; and
   (d) a plurality of barbs formed on the outer surface of the post, the plurality of barbs having tips angled upwardly toward the closed top.

5. The device of claim 4 wherein the device is formed of a polymer material selected from the group of materials consisting of polyureas, polyurethanes, poly(ethylene/-vinyl acetate), polyvinylchloride, polyesters, polyamides, polycarbonate, polyethylene, polypropylene, polystyrenes, polytetrafluoroethylene, polyhydroxyalkanoates, silicone, and combinations thereof.

* * * * *